United States Patent [19]

Katz

[11] Patent Number: 4,586,490

[45] Date of Patent: May 6, 1986

[54] NEEDLE INSERTING INSTRUMENT MEANS FOR INTERSTITIAL RADIOTHERAPY

[76] Inventor: Harry R. Katz, 315 Evergreen Rd., Jenkintown, Pa. 19046

[21] Appl. No.: 583,585

[22] Filed: Feb. 27, 1984

[51] Int. Cl.⁴ .............................................. A61B 17/06
[52] U.S. Cl. ..................................................... 128/1.1
[58] Field of Search ............... 128/303 R, 303 B, 1.1, 128/321, 322, 340, 346, 339, 1.2; 604/60, 61, 62, 63, 64, 116, 117, 173, 272, 273, 274, 46

[56] References Cited

U.S. PATENT DOCUMENTS

| | | | |
|---|---|---|---|
| 2,617,418 | 11/1952 | Del Pico | 604/46 |
| 3,019,790 | 2/1962 | Militana | 128/346 |
| 3,086,530 | 4/1963 | Groom | 604/46 |
| 3,467,096 | 9/1969 | Horn | 604/173 |
| 3,595,231 | 7/1971 | Pistor | 604/173 |
| 3,779,248 | 12/1973 | Karman | 128/346 |
| 4,269,190 | 5/1981 | Behney | 128/346 |

OTHER PUBLICATIONS

"A Method of Interstitial Tonsillo–Palatine Implants" by Goffinet et al., Int. J. Radiation Oncology Biol. Phys. 1977, vol. 2 pp. 155–162.
Radium Accessories—Radium Chemical Company, Inc.
"Sklar Products—Surgical Instruments & Pressure Apparatus" 18th Edition 1973 J. Sklar Mfg. Co. pp. 67 and 100.

Primary Examiner—Kyle L. Howell
Assistant Examiner—David Shay
Attorney, Agent, or Firm—Jacob Trachtman

[57] ABSTRACT

An instrument for inserting a plurality of hollow needles into a body for interstitial radiotherapy comprising a unit having a pair of elongated members each having first and second ends and providing clamping portion at the first ends and a handle at the second ends. The members are pivotally connected intermediate their ends for movement between closed and opened conditions by actuation of the handle, and the clamping portion engages the needles when the members are in the closed condition and disengages and releases the needles when the members are in the opened condition. Needle retaining means secured with the unit slidably receives the plurality of needles which are controllably engaged by the clamping portion of the unit and includes a needle aligning device having a plurality of openings for positioning the needles in parallel relation to each other within the same plane and stop for engaging the back ends of the needles for adjusting the extension of their sharpened front ends beyond the clamping portion.

20 Claims, 6 Drawing Figures

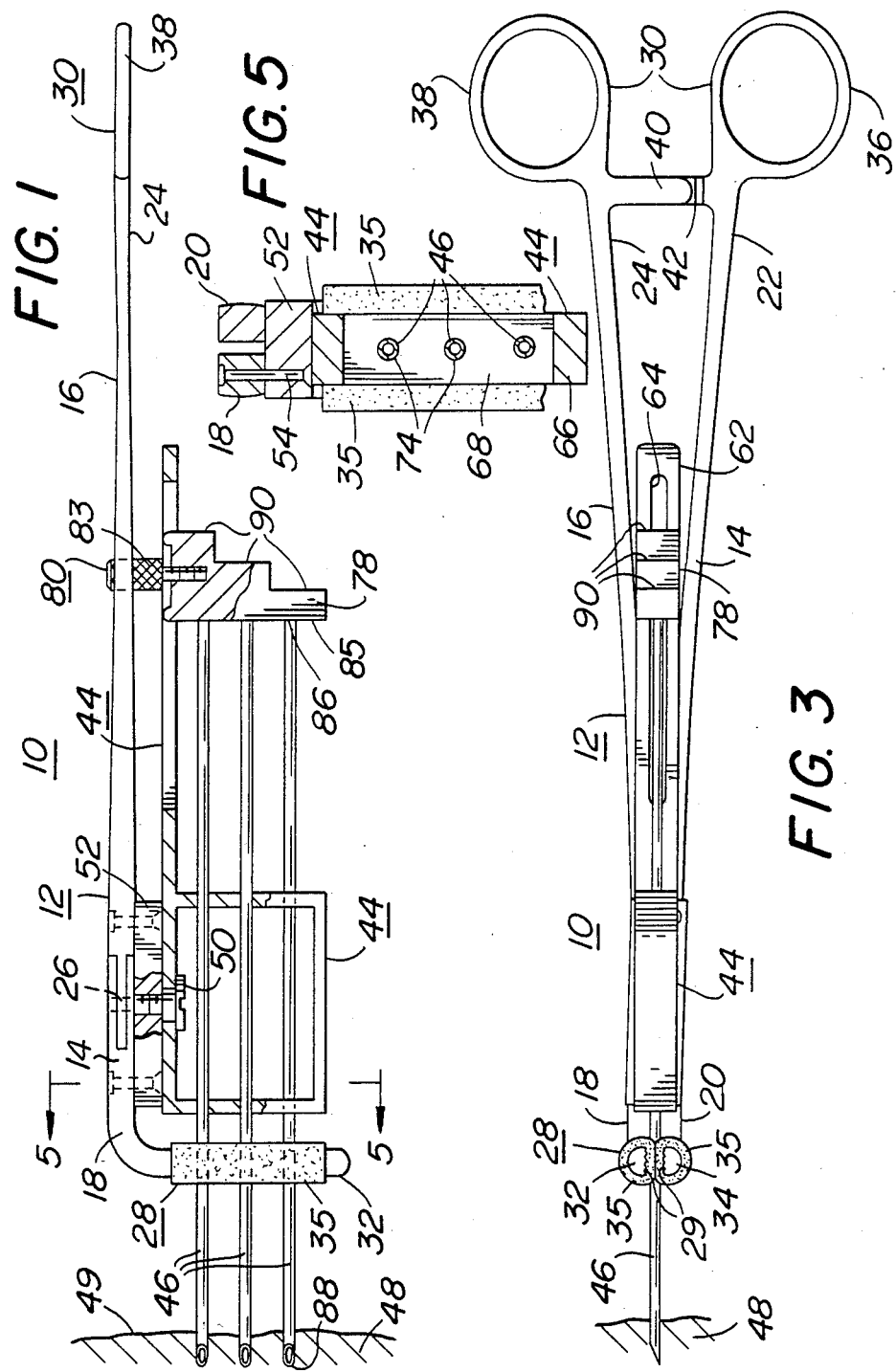

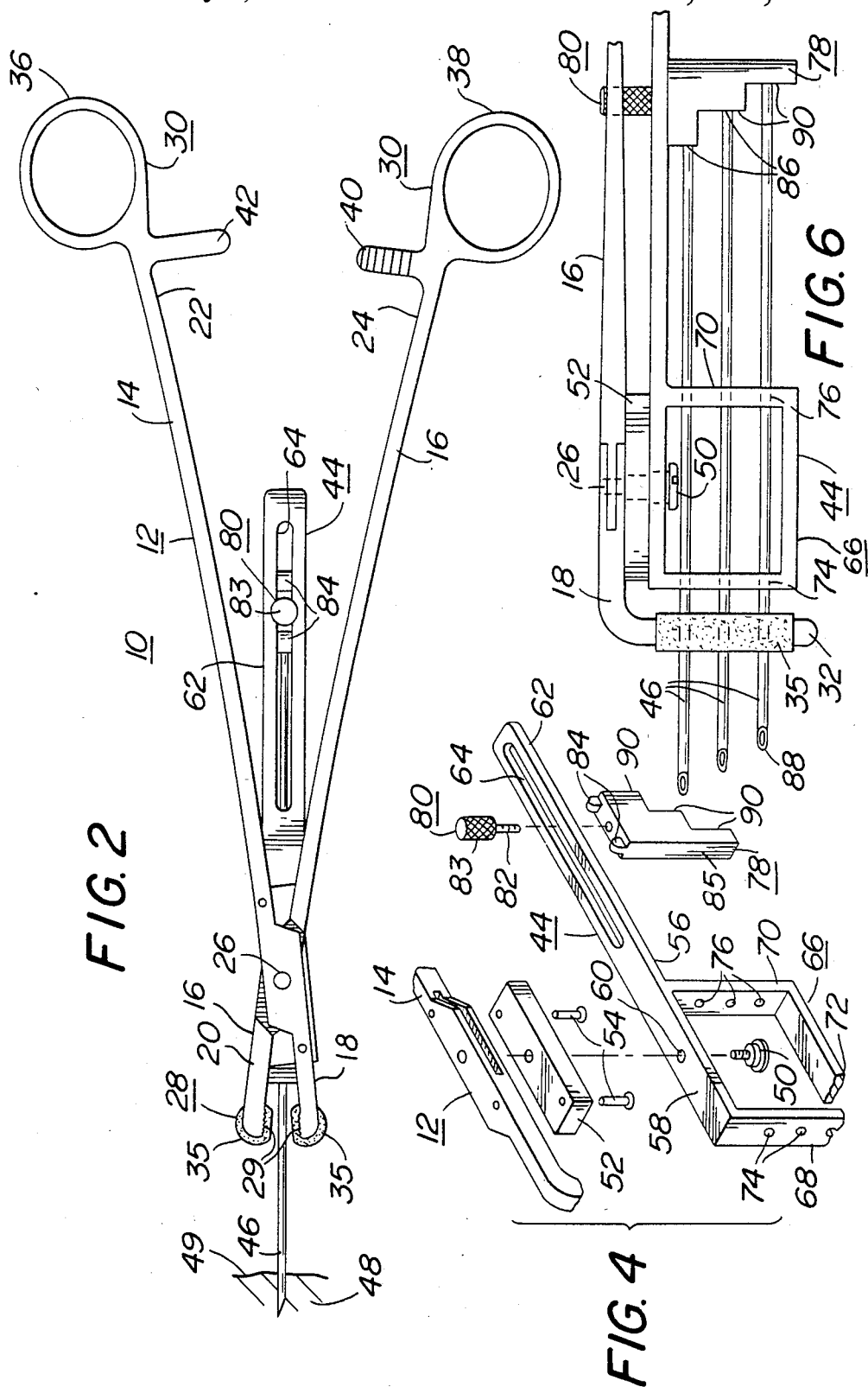

NEEDLE INSERTING INSTRUMENT MEANS FOR INTERSTITIAL RADIOTHERAPY

BACKGROUND OF THE INVENTION

The present invention relates to an instrument means for use in radiotherapy, and more particularly to an instrument means for inserting a plurality of parallel hollow stainless steel needles into the body for interstitial implanation of radioactive materials during the treatment of malignant tumors.

The interstitial implantation of radioactive isotopes is a well established technique for the treatment of malignant tumors. Short lengths of a radioactive source, such as Iridium-192, are linearly arranged within thin walled plastic tubes to form "ribbons." These ribbons are used as temporary interstitial implants in a wide variety of clinical situations. Each ribbon, which is very flexible, must be inserted into the body with the aid of a rigid trocar, in the form of a hollow stainless steel needle, which is sharpened at one end for piercing the skin and tumor bearing tissue. An array of the hollow needles are first inserted into the tissues to be implanted. The needles are typically spaced evenly throughout the volume of tissue to be irradiated, and are parallel to one another to avoid areas of underdose or overdose. After the hollow needles have been inserted, ribbons of radioactive sources are inserted into the bores of the needles to a position determined by the location of the tumor bearing tissue. In certain clinical situations the needles may be left in place in the body, along with the sources, for the duration of the implant, after which both are removed. In other situations, the needles may be pulled out of the body, leaving behind only the ribbon sources for the duration of the implant.

For example, when the implantation is for tumors of the head and neck area, the needles are usually inserted in an array of one or more planes, each plane comprising typically two to four parallel and equally spaced needles. In performing such an implant, the insertion of multiple parallel needles in such planes is difficult without the use of external guidance, such as provided by a template.

In the past templates consisting of rigid plates provided with a series of parallel guide holes have been applied to the body surface for inserting needles in parallel paths into the body. However these external templates are only useful on relatively flat surfaces of the body, where the entire face of the template can be readily secured and held in contact with the skin surface for stability and accuracy in guiding the needles in the desired direction. They are not suited for use on irregular or contoured body surfaces such as in the head and neck areas. Since the prior art templates are designed for placement directly on the skin surface for percutaneous implants, they are also not suitable for use when needles must be inserted directly into open body cavities to irradiate tissues adjacent to or within these cavities. Even if such templates were to be used in areas with irregular body surface contours or within body cavities, they would have to be manually retained in position, thereby preventing the use of bimanual stereotactic guidance by the radiotherapist in the insertion of the needles. It would also make the insertion of multiple needles cumbersome, especially within the body cavities where space is limited.

A needle insertion instrument means for interstitial radiotherapy which permits the simultaneous insertion in difficult areas of a plurality of spaced parallel needles in a single plane, and requires only one hand for its operation while permitting the other hand to remain free to support the area of the body being implanted for providing continuous bimanual stereotactic guidance of the needles as they are advanced into the body, would be of great advantage in allowing easier, more accurate, and faster insertion of such needles.

SUMMARY OF THE INVENTION

Accordingly, a principal object of the invention is to provide a new and improved instrument means for inserting a plurality of parallel needles into the body for interstitial radiotherapy which overcomes deficiencies of devices previously employed.

Another object of the invention is to provide a new and improved instrument means for simultaneously inserting a plurality of parallel needles in the same plane into the body for interstitial radiotherapy.

A further object of the invention is to provide a new and improved instrument means for simultaneously inserting a plurality of parallel needles into the body for interstitial radiotherapy which may be moved in retrograde fashion along the implant needles which are being advanced into the body, for permitting long needles to be inserted without risk of bending.

A further object of the invention is to provide a new and improved instrument means for simultaneously inserting a plurality of parallel needles into the body for interstitial radiotherapy which permits insertion of the implant needles in a closely spaced array, in areas of irregular surface contour, and within the body where use of separate template means for parallel guidance would be extremely difficult.

A further object of the invention is to provide a new and improved instrument means for simultaneously inserting a plurality of parallel needles into the body for interstitial radiotherapy using one hand, while permitting the other hand to be used to support the area of the body being implanted and permitting continuous bimanual stereotactic guidance of the needles as they are inserted into the body towards their intended locations.

A further object of the invention is to provide a new and improved instrument means for simultaneously inserting a plurality of parallel needles into the body for interstitial radiotherapy which has interchangeable components for permitting its use with needles of different diameters, lengths, and spacings.

A further object of the invention is to provide a new and improved instrument means for simultaneously inserting a plurality of parallel needles into the body for interstitial radiotherapy, which is simple in design and construction, and permits ready assembly, disassembly, cleaning and sterilization for each use.

The above objects as well as many others are achieved by providing an instrument means comprising a unit having clamping and handle means for controllably engaging and securing with the unit a plurality of needles to be inserted into the body and needle retaining means secured with the unit for slidably receiving and positioning the plurality of needles which are controllably engaged by the clamping means of the unit. The unit comprises a pair of elongated members each having first and second ends with the clamping means being provided at the first ends and the handle means at the second ends. The members are pivotally connected intermediate their ends for movement between closed and opened conditions by actuation of the handle means. The clamping means engages the needles when the members are in the closed condition and disengages and releases the needles when the members are in the opened condition.

The first ends of each of the members have a portion bent to extend transversely to the longitudinal direction of its member for providing the clamping means and move towards each other for engaging the needles when the members are actuated toward the closed condition and move away from each other for disengaging the needles when the members are actuated toward the opened condition. The handle means provided by the second ends of the members receive fingers of one hand for actuating the members between the closed and opened conditions and for controlling the movement of the instrument means during the insertion of the needles into the body. The handle means of the unit has releasable securing means for locking the members after movement by actuation of the handle means towards the closed condition for keeping the needles clamped between the first ends of the members until released.

The needle retaining means positions the needles to extend between and transverse to the bent portions of the first ends of the members for being clamped therewith. The retaining means includes a needle aligning device having a plurality of openings for positioning the needles in parallel relation to each other within the same plane, and stop means for engaging the back ends of each of the needles for adjusting the extension of the sharpened front ends of each of the needles beyond the clamping means. The stop means is positionable toward and away from the guide means for adjusting the extension of the front end of each of the needles beyond the clamping means and is positionable for selectively providing equal and unequal extensions of the front ends of the needles beyond the clamping means. The retaining means is pivotally joined with the unit proximate to the pivotal connection of the members and has a portion extending between and engaging the members for limiting the pivotal movement of the retaining means and permitting angular adjustment of the needles between the first ends of the members as the members are moved toward the closed condition.

Still other objects, features, and advantages of the invention will be apparent to those skilled in the art from the following detailed description, together with the accompanying drawing and appended claims.

DESCRIPTION OF THE DRAWING

For a fuller understanding of the nature and objects of the invention, reference should be made to the following detailed description taken in connection with the accompanying drawing, in which:

FIG. 1 is a side elevational view with portions broken away of an instrument means embodying the invention for inserting a plurality of parallel hollow needles into the body for interstitial radiotherapy.

FIG. 2 is a top plan view of the instrument means of FIG. 1 shown in its opened condition, FIG. 3 is a bottom plan view of the instrument means of FIG. 1 shown in its closed condition, FIG. 4 is an exploded perspective view illustrating the needle retaining means of the instrument means of FIG. 1, FIG. 5 is an enlarged sectional view taken on the line 5—5 of FIG. 1, and FIG. 6 is a side elevational view of the needle retaining means shown in FIG. 1 illustrating the stop means positioned for unequally extending the plurality of needles.

Like reference numerals designate like parts throughout the several views.

DETAILED DESCRIPTION

Refer to the figures, which illustrate an instrument means 10 for use in interstitial radiotherapy embodying the invention. The instrument means 10 which is used for simultaneously inserting a plurality of hollow needles into a body, comprises a unit 12 having a pair of elongated members 14 and 16 each with a first front end 18, 20 and a second rear end 22, 24. The members 14, 16 are pivotally secured together by a pin 26 located closer to the front ends 18, 20 than the rear ends 22, 24. Clamping means 28 is provided by the bent portions 32 and 34 of the front ends 18 and 20, each of which extends transversely to the elongated direction of its member 14, 16. The bent portions 32, 34 each have a flattened serrated surface 29 positioned opposite to each other which form jaws for engaging the needles 46 therebetween. Respective tubular rubber sleeves 35 are received over the portions 32, 34 and firmly retained thereon by the serrated surfaces for resiliently engaging and minimizing damage to needles which are secured by the clamping means 28. The handle means 30 is provided at the rear ends 22, 24 of the members 14 and 16 by enlarged portions 36, 38, each of which provides an opening for receiving a finger of one hand for actuating the unit 12 between closed and opened conditions. When the portions 36, 38 of the handle means 30 are moved apart, the portions 32, 34 of the clamping means 28 move away from each other placing the unit in its opened condition. As the portions 36, 38 are moved toward each other the portions 32, 34 also move together for placing the unit 12 in its closed clamping condition. The rear ends 22, 24 are also provided with respective interengageable serrated extending portions 40, 42 for releasably securing together the rear ends 22, 24 when they are moved towards each other for placing the instrument means 10 in its closed condition. The portions 40, 42 can be easily disengaged for allowing the rear ends 22, 24 to move away from each other for placing the instrument means 10 in its opened condition.

A needle retaining means 44 which is secured with the unit 12 slidably receives and retains a plurality of needles 46 for insertion into the tissue of a body 48 through its skin or surface 49. As shown in FIG. 4, the needle retaining means 44 is pivotally secured to the unit 12 by a pin 50 which threadedly engages a rectangular plate 52 attached by rivets 54 to the member 16. The plate 52 is positioned below the pivot pin 26 of the unit 12, and provides for the retaining means 44 to pivot about the same axis as the members 14 and 16. A thin elongated portion 56 of the needle retaining means 44 has a forward end 58 containing the opening 60 through which the pin 50 passes and a rear end 62 with an elongated slot 64. The needle retaining means 44 also includes a needle aligning device 66 of rectangular form having a pair of spaced vertical side elements 68, 70 extending downwardly from the end 58 of the elongated portion 56 and a bottom horizontal element 72 connecting the lower ends of the side elements 68, 70. The side element 68 has a plurality of vertically spaced openings 74 aligned with openings 76 of the side element 70 for slidably receiving through each pair of the aligned openings a respective one of the plurality of needles 46 and positioning them in parallel relation in the same plane.

The needle retaining means 44 also has a stop means 78 adjustably secured with the end 62 of the elongated portion 56 by a threaded screw means 80. The lower threaded portion 82 of the screw means 80 is of reduced size with respect to the top portion 83 and extends through the slot 64 of the elongated portion 56 to threadedly engage the stop means 78. The screw means 80 secures the stop means 78 to extend downwardly from the bottom side of the end 62. The top portion 83 of the screw means extends upwardly between the members 14, 16 at a location intermediate the pivot pin 26 and the handle means 30 for limiting the angular movement of the needle retaining means 44 about its pin 50.

The top of the stop means 78 has projections 84 which extend upwardly into the slot 64 for aligning the stop means 78 when the screw means 80 is tightened, and allows the stop means 78 to slide along the slot 64 when the screw means 80 is loosened for adjusting its position with respect to the aligning device 66 of the needle retaining means 44. One side of the stop means 78 has a plane vertical surface 85 for engaging the rear ends 86 of each of the needles 46 for aligning their front sharpened ends 88 to extend an equal distance beyond the clamping means 28 of the unit 12. The amount to which the needles 46 extend beyond the clamping means 28 may be adjusted by loosening the screw means 80 and sliding the stop means 78 along the slot 64 to the desired position and retightening the screw means 80. The side of the stop means 78 opposite its surface 85 is provided with a plurality of stepped vertical surfaces 90, which engage the ends 86 of the needles 46 when the stop means 78 is positioned as shown in FIG. 6 by loosening the screw means 80 and reversing the stop means 78. When so positioned the front pointed ends 88 of the needles extend different or unequal distances beyond the clamping means 28. This arrangement may be desirable when the needles 46 are to pierce skin or dense tissue requiring greater force to be concentrated on a single needle for easier insertion of each of the sharpened ends of the needles.

In operation, the instrument means 10 is placed in its opened condition as shown in FIG. 2, and the needles 46 are inserted through respective pairs of aligned openings 74, 76 of the needle aligning device 66 with the needle back ends 86 engaging the stop means 78. The stop means 78 is adjusted to provide for a limited extension of the front ends 88 of the needles beyond the clamping means 28 of the instrument means 10 to provide the control and stiffness desired for inserting the needles. The handle means 30 which receives fingers of one hand can now be manipulated for placing the instrument means 10 in its closed condition as shown in FIG. 3. With the needles 46 securely engaged by the clamping means 28, the instrument means 10 is locked in its closed condition by the interengagement of the serrated extending portions 40, 42 of the handle means 30 as also shown in FIG. 3.

Since the front ends 88 of the needles 46 are positioned only a small predetermined distance in front of the clamping means 28 and are firmly secured therewith, they are substantially rigid and not subject to flexing when force is applied for inserting the needles 46 into the body tissue. The sharpened ends 88 of the needles are placed in position on the skin 49 of a body 48 and force is exerted by the hand engaging the handle means 30 for moving the needles into the tissue of the body. The needles are advanced into the body until the skin or surface 49 closely approaches or touches the clamping means 28. At this time, the instrument means 10 is placed in its opened condition by releasing the serrated portions 40, 42 of the handle means 30 and moving the rear ends 22, 24 of the members 14, 16 away from each other. This results in the separation of the portions 32, 34 of the clamping means 28, allowing the instrument means 10 to be slid along the needles 46 in the retrograde direction and then again placed in the closed condition after the clamping means 28 is spaced a small distance away from the skin or surface 49 of the body 48. The needles 46 are then again advanced into the body for a short distance as before followed by the retrograde movement. Such advancement and retrograde movements are continued until the needles are inserted to the depth desired. The instrument means 10 may then be disengaged and removed to leave the needles inserted in the tissue of the body 48 in spaced parallel relationship within a single plane. If desired, another one or more sets of parallel needles may be inserted into the tissue in spaced relationship to the implanted needles by carrying out the same procedure.

The instrument means 10 permits the radiotherapist to simultaneously insert a plurality of hollow needles into the tissue of a body in spaced parallel relationship by use of only one hand. This is achieved by alternately clamping the needles with the instrument means 10 and incrementally advancing them into the body and then releasing the needles and moving the instrument means 10 along the needles in retrograde fashion until the needles are inserted into the body at the location and to the extent desired. Since only one hand is required for manipulating the instrument means 10, the other hand may be used to provide continuous bimanual stereotactic guidance of the needles as they are advanced into and positioned within the body.

Since it may be desirable to use needles of smaller or larger diameters, and different lengths and spacings, the needle retaining means 44 may be easily detached from the unit 12 by removing the pin 50, and replaced by another needle retaining means 44 providing the desired openings and spacings. The pivotal connection of the needle retaining means 44 to the unit 12 serves to accomodate needles 46 of different diameters by adjusted angular position of the needles for centering them between the portions 32, 34 of the clamping means 28.

It will of course, be understood that the description and drawing herein are illustrative merely, and that various modifications and changes may be made in the instrument disclosed without departing from the spirit of the invention.

What is claimed is:

1. An instrument means for concurrently inserting a plurality of hollow needles into a body for interstitial radiotherapy comprising a unit having handle means and providing clamping means for controllably alternately engaging and securing with the unit and releasing from the unit a plurality of needles which are to be inserted into a body by incremental advancements, the clamping means being released for moving the unit back along the needles after each advancement and being clamped for further advancing the needles, and needle retaining means secured with the unit spaced from said clamping means for slidably receiving and positioning the plurality of needles while they are controllably engaged and secured with the unit and released from the unit by the clamping means of the unit during their incremental advancements.

2. The instrument means of claim 1 in which the unit comprises a pair of elongated members each having first and second ends with the clamping means being provided at the first ends and the handle means at the second ends, the members are pivotally connected intermediate their ends for movement between closed and opened conditions by actuation of the handle means, and the clamping means engages the needles when the members are in the closed condition and disengages and releases the needles when the members are in the opened condition.

3. The instrument means of claim 2 in which at least a portion of the first ends of each of the members extends transversely to the longitudinal direction of its member for providing the clamping means, the first ends move toward each other for engaging the needles when the members are actuated toward the closed condition and move away from each other for disengaging the needles when the members are actuated toward the opened condition, and the needle retaining means includes means for positioning the needles to extend substantially in the longitudinal direction intermediate the members and between and transverse to the first ends of the members for being clamped therewith.

4. The instrument means of claim 3 in which the handle means provided by the second ends of the members includes means for receiving the fingers of one hand for actuating of the members between the closed and opened conditions and for controlling the movement of the instrument means during the insertion of the needles into the body.

5. The instrument means of claim 1 in which the retaining means includes means for positioning the needles in parallel relation to each other.

6. The instrument means of claim 5 in which the retaining means includes a needle aligning device having a plurality of openings for positioning the needles in parallel relation to each other within the same plane.

7. The instrument means of claim 6 in which the retaining means includes stop means for engaging the back end of each of the needles and initially adjusting the extension of the sharpened front end of each of the needles beyond the clamping means.

8. The instrument means of claim 7 in which the unit comprises a pair of elongated members each having first and second ends and providing the clamping means at the first ends and the handle means at the second ends, the members are pivotally connected intermediate their ends for movement between closed and opened conditions by actuation of the handle means, and the clamping means engages the needles when the members are in their closed condition and disengages and releases the needles when the members are in the opened condition.

9. The instrument means of claim 8 in which at least a portion of the first ends of each of the members extends transversely to the longitudinal direction of its member for providing the clamping means, the first ends move toward each other for engaging the needles when the members are actuated toward the closed condition and move away from each other for disengaging the needles when the members are actuated toward the opened condition, and the needle retaining means positions the needles to extend between and transverse to the first ends of the members for being clamped therewith.

10. The instrument means of claim 9 in which the handle means provided by the second ends of the members includes means for receiving the fingers of one hand for actuating of the members between the closed and opened conditions and for controlling the movement of the instrument during the insertion of the needles into the body.

11. The instrument means of claim 10 in which the stop means is positionable toward and away from the needle aligning device for adjusting the extension of the front end of each of the needles beyond the clamping means, the first ends of the members each receive a resilient sleeve thereabout for engaging the needles, the aligning device is detachably secured with the unit, and the stop means is positionable toward and away from the clamping means for adjusting the extension of the front ends of the needles beyond the clamping means and for selectively providing equal and unequal extensions of the front ends of the needles beyond the clamping means.

12. The instrument means of claim 3 in which the retaining means is pivotally secured with the elongated members for permitting angular adjustment of the needles between the first ends of the members as the members move toward the closed condition.

13. The instrument means of claim 12 in which the retaining means positions the needles parallel to each other within the same plane.

14. The instrument means of claim 13 in which the retaining means includes a needle aligning device having a plurality of openings for receiving and positioning the needles.

15. The instrument means of claim 14 in which the retaining means includes stop means for engaging the back end of each of the needles and adjusting the extension of the sharpened front end of each of the needles beyond the clamping means.

16. The instrument means of claim 15 in which the stop means is positionable toward and away from the needle aligning device for adjusting the extension of the needles beyond the clamping means.

17. The instrument means of claim 16 in which the stop means has a surface for engaging the back ends of the needles providing for equal extension of each of the front ends of the needles beyond the clamping means.

18. The instrument means of claim 16 in which the stop means has a surface for engaging the back ends of the needles providing for unequal extension of each of the front ends of the needles beyond the clamping means.

19. The instrument means of claim 16 in which at least a portion of the first ends of the members each receive a resilient clamping sleeve thereabout for gripping the needles, the handle means provided by the second ends of the members include means for receiving the fingers of one hand for actuating the members between their closed and opened conditions and for controlling the movement of the instrument during the insertion of the needles into the body, and the retaining means is pivotally joined with the unit proximate to the pivotal connection of the members and has a portion extending between and engaging the members for limiting the pivotal movement of the retaining means and permitting the angular adjustment of the needles between the first ends of the members as the members move toward the closed condition.

20. The instrument means of claim 19 in which the handle means of the unit has releasable securing means for locking the members after movement by actuation of the handle means toward the closed condition for keeping the needles clamped between the first ends of the members.

* * * * *